(12) United States Patent
Ma

(10) Patent No.: US 9,823,628 B2
(45) Date of Patent: Nov. 21, 2017

(54) LABORATORY SYSTEM

(71) Applicant: Tecan Trading AG, Mannedorf (CH)

(72) Inventor: Mark Ma, San Jose, CA (US)

(73) Assignee: Tecan Trading AG, Mannedorf (CH)

( * ) Notice: Subject to any disclaimer, the term of this patent is extended or adjusted under 35 U.S.C. 154(b) by 991 days.

(21) Appl. No.: 13/739,455

(22) Filed: Jan. 11, 2013

(65) Prior Publication Data

US 2014/0200683 A1   Jul. 17, 2014

(51) Int. Cl.
  *G05B 15/02*  (2006.01)
  *G05B 19/042* (2006.01)
  *G01N 35/10*  (2006.01)
  *B01L 3/02*   (2006.01)

(52) U.S. Cl.
  CPC .......... *G05B 15/02* (2013.01); *G01N 35/109* (2013.01); *G01N 35/1011* (2013.01); *G05B 19/0426* (2013.01); *B01L 3/0293* (2013.01); *G01N 2035/1076* (2013.01); *G05B 2219/25482* (2013.01)

(58) Field of Classification Search
  None
  See application file for complete search history.

(56) References Cited

U.S. PATENT DOCUMENTS

| 4,953,075 A | 8/1990 | Nau et al. |
| 5,206,568 A | 4/1993 | Bjoernson et al. |
| 2003/0017085 A1 | 1/2003 | Kercso et al. |
| 2003/0078695 A1* | 4/2003 | Takagi et al. ................. 700/245 |
| 2005/0159982 A1* | 7/2005 | Showalter ............. G06F 19/366 705/2 |

OTHER PUBLICATIONS

M. K. Senehi et al., "Manufacaturing Systems Integration—Control Entity Interface Document", Jun. 1991, United States Department of Commerce, National Institute of Standards and Technology, Manufacturing Engineering Laboratory, NISTIR 4626, Cover/Title, p. i-45.*

International Preliminary Report on Patentability for PCT/EP2014/050278 filed Jan. 9, 2014.

* cited by examiner

*Primary Examiner* — Mohammad Ali
*Assistant Examiner* — Saad M Kabir
(74) *Attorney, Agent, or Firm* — Notaro, Michalos & Zaccaria P.C.

(57) ABSTRACT

A laboratory system and a method for controlling a laboratory system comprises multiple subsystems; each subsystem being configured to receive and carry out a command; and a master control device configured to process command groups and/or command(s) within the same command group simultaneously; to process command groups and/or command(s) of different command groups sequentially; and within a command group, to process command group(s) and/or command(s) grouped into a command group before processing other commands command group(s) and/or command(s).

15 Claims, 4 Drawing Sheets

LABORATORY SYSTEM

FIELD OF THE INVENTION

The present invention relates to a laboratory system comprising multiple subsystems configured to receive and carry out commands.

BACKGROUND OF THE INVENTION

When addressing commands to different subsystems of a laboratory system, synchronization and coordination among subsystems are required to either avoid device collisions and/or to improve overall throughput and efficiency.

This has been solved in the past by predefining relations between subsystems. However, predefining such relations using system configurations or subsystem enquiries during operation of the system (e.g. motion of a robotic arm, activation of an actuator, status report) is either limited in capabilities and time consuming or requires dealing with multiple subsystem responses and thus increases the complexity of system control design.

Some known systems employ a command format design, wherein commands sent to a subsystem to be carried out followed by the subsystem reporting back a response upon completion of the command.

In addition a command format design has been in use, wherein commands sent to the subsystem may comprise a concatenation of instructions to be executed sequentially, one after the other. Concatenation of instructions thus allowing the subsystem to perform multiple operations sequentially prior to reporting a response. To address commands to other subsystems, the same method is performed addressing different subsystems (for example by using a subsystem identifier). Since there are no predefined relations specified among the subsystems, the user or higher level control system is responsible for coordinating the movements and manage all of the individual responses from the subsystems. As a conclusion, the complexity of the system increases substantially with more subsystems introduced into a system.

The problem is further aggravated in systems where subsystems are often added, removed or reconfigured.

TECHNICAL PROBLEM TO BE SOLVED

The objective of the present invention is thus to provide a laboratory system—such as a laboratory liquid handling system—overcoming these disadvantages and providing a flexible and efficient system ensuring that subsystem/device collisions are avoided without the need to predefine/re-define relations between each subsystem upon each reconfiguration or change of the subsystems within the laboratory system, allowing the coordination of the subsystems to be defined dynamically.

A further objective of the present invention is to provide a method for controlling a laboratory system in a flexible and efficient manner while ensuring that subsystem/device collisions are avoided without the need to predefine/re-define relations between each subsystem upon each reconfiguration or change of the subsystems within the laboratory system, allowing the coordination of the subsystems to be defined dynamically.

SUMMARY OF THE INVENTION

The above identified objectives of the present invention are solved by a laboratory system comprising multiple subsystems—each subsystem being configured to receive and carry out a command—and a master control device configured to process a command string and to transmit command(s) to a corresponding subsystem. The command string comprises one or more command group(s) and/or one or more command(s). In other words the command(s) and command group(s) may be nested on multiple levels of grouping.

The sequence of expected subsystem operations are encoded according to the present invention in a command string transmitted to a master control device. The coordination/synchronization of subsystems is defined dynamically via this command string. For processing the command string of the above format, the master control device is configured as follows:

to simultaneously process command groups(s) prior to simultaneously transmitting command(s) within the same command group; and to sequentially process command group(s) and/or transmit command(s) not within a same command group.

The master control device processes the input command string (be it a group or individual command) in a recursive manner, each time going one level inside the nested groups of commands, transmitting individual commands to the respective subsystem when a level is reached where the command(s) is/are by themselves, i.e. not grouped.

The above identified further objective of the present invention is solved by a method for controlling a laboratory system with multiple subsystems configured to receive and carry out a command. Said control being implemented by transmitting a command string to a master control device of the laboratory system to be processed, the method comprising the steps of:

I) grouping command(s) and/or command group(s) to be processed simultaneously into respective command group(s);

II) concatenating command(s) and/or command group(s) to be processed sequentially; and III) grouping command(s) and/or command group(s) with higher execution priority into respective command group(s).

The method of control "encodes" the commands in a recursive manner, each time grouping the command(s) and/or command group(s) one level "deeper" and encoding individual commands to be executed by the respective subsystem by themselves, i.e. not grouped. By grouping command(s) and/or command group(s) with higher execution priority into respective command group(s), the method of the present invention allows "encoding" of the desired sequence/precedence of execution into the command string.

ADVANTAGEOUS EFFECTS

One of the most important advantages of the present invention is that the coordination/synchronization of subsystems is defined dynamically via the command string transmitted to the master control device of the laboratory system. No predefined relation among the subsystems is required. The overall result of the processed command string can be reported by the master control device, thus eliminating multiple intermediate responses reported by the subsystems during the command string execution.

BRIEF DESCRIPTION OF THE DRAWINGS

Further characteristics and advantages of the invention will in the following be described in detail by means of the description and by making reference to the drawings. Which show.

Figure 1:
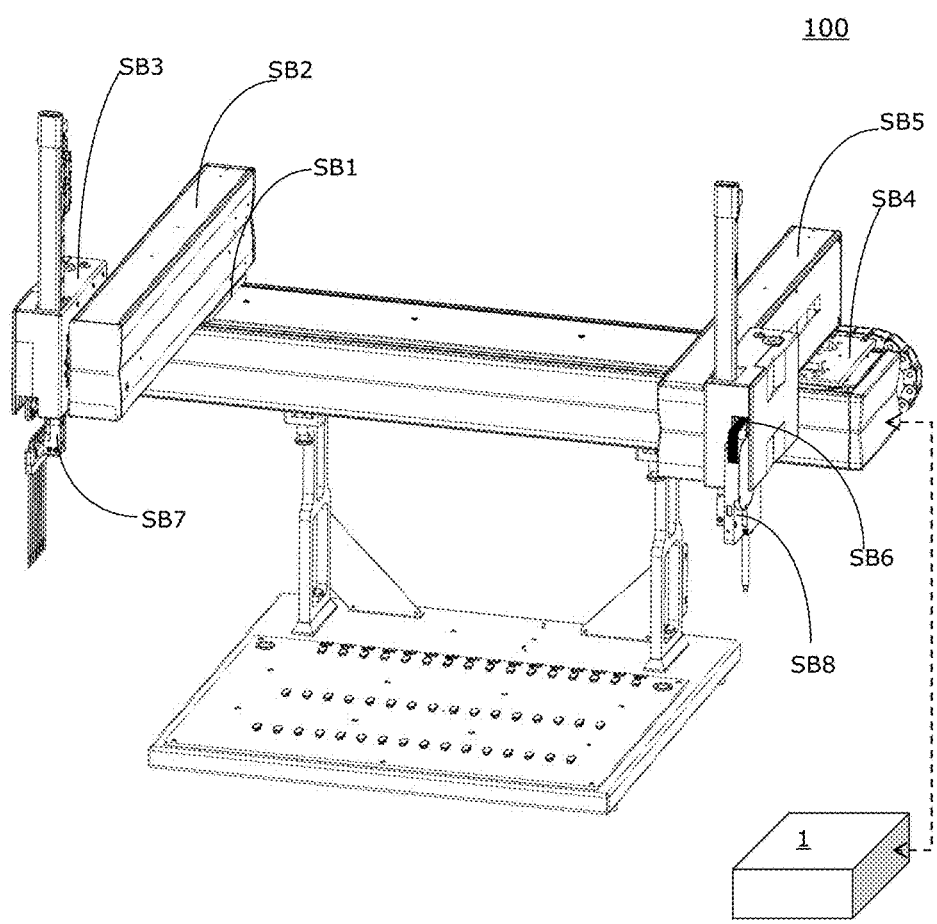
FIG. 1 a perspective view of a robotic system as an exemplary laboratory system according to the present invention.

Note: The figures are not drawn to scale, are provided as illustration only and serve only for better understanding but not for defining the scope of the invention. No limitations of any features of the invention should be implied form these figures.

DESCRIPTION OF PREFERRED EMBODIMENTS

Certain terms will be used in this patent application, the formulation of which should not be interpreted to be limited by the specific term chosen, but as to relate to the general concept behind the specific term.

The term laboratory system shall be used in its broadest sense comprising but not limited to laboratory robotic systems, such as for example liquid handling systems, diluters etc. The term subsystem, in relation with the laboratory system, shall be used to refer to any addressable component or collection of components of the laboratory system comprising but not limited to diluters; actuators; sensors; pumps; indicating devices; etc. In the embodiments of the present invention illustrated on FIGS. 1 and 2, the subsystems are robotic arms SB1 to SB6 of a six-axis robotic system (laboratory system 100), respectively two attached devices SB7 and SB8.

The term master control device shall be used to refer to any type of hardware or software component of a laboratory system suitable to receive and process strings of commands and to communicate with said subsystems, i.e. transmit commands respectively receive response signals such as OK respectively error responses.

The term instruction I shall be used to refer to any singular or collective instruction I any of the subsystems SB or devices within a subsystem SB of the laboratory system 100 are able to receive/interpret and execute. For example in the case of robotic arms SB1 to SB6, such instructions I comprise but are not limited to instructions for linear movement, instructions associated with a parameter such as distance. Another exemplary instruction I would be the initialization of subsystem (an instruction which would have no parameter(s)). In the case of attached devices like SB7 or SB8 such as a pipetting device, the instruction I might be "Pickup" with an instruction parameter IP defining the amount to be sucked in.

The term command C shall be used to refer to an individual instruction I or a concatenation of instructions I associated to a subsystem, the command C preferably comprising a subsystem identifier SI.

The term command group CG shall refer a collection or group of command(s) C but may comprise nested command groups CG on multiple levels. A command string CS may comprise only one command group CG or a concatenation of command(s) C and/or command group(s) CG or any combination thereof. In other words each command group CG is a command string CS but not each command string CS is a command group CG.

The term "top level" group when referring to command group(s) or command(s) shall mean the single topmost level of grouping within the command string to which it refers to disregarding groupings below this top level.

When referring to the inner command(s) C and/or command group(s) CG "within" a command group CG or command string CS, in the context of the present invention, the collection of command(s) C and/or command group(s) CG shall be meant which is contained one "grouping level below".

The term processing in relationship with a command string CS respectively command group CG comprises but is not limited to identifying individual command(s) and/or command group(s) CG within the command group CG being processed; recursive processing of the command group(s) CG contained therein respectively transmission of command(s) C to the corresponding subsystem SB.

The term prior shall mean that the next step (processing of a command group(s) or transmission of command(s)) is started only once the previous step completed. In other words the term prior imposes a sequentially of a particular order.

The term simultaneous when referring to the processing of command groups CG respectively transmission of commands C shall be understood as simultaneous as far as the functionality of the system is concerned. Depending on the implementation of the control device (e.g. single core system) and of the transmission between components (e.g. serial/bus communication protocol being used) of the laboratory systems, the simultaneity might be an apparent simultaneity simulated by the underlying hardware and/or software.

The term sequential when referring to the processing of command groups CG respectively transmission of commands C shall be understood as the master control device "waiting" for the previous command group CG to be processed respectively the previously transmitted command C to be carried out, before processing the next command group CG respectively transmitting the next command C.

The term delimiter shall be interpreted in its broadest sense, any single element (such as character; binary sequence; signal level) of the alphabet of representation of may be used as delimiter.

The sequence of expected subsystem operations are encoded according to the present invention in a command string CS transmitted to a master control device 1. The coordination/synchronization of subsystems SB is defined dynamically via this command string CS. For processing the command string CS of the above format, the master control device 1 is configured as follows:
- to simultaneously process command group(s) CG prior to simultaneously transmitting command(s) C within the same command group CG; and
- to sequentially process command group(s) CG respectively transmit command(s) C not within the same command group CG.

In other words, the master control device 1 of the present invention processes a command string CS comprising a command(s) C and/or command group(s) CG and each command group CG comprising a command(s) C and/or command group(s) CG as follows:

a) The master control device 1 is configured to verify whether the command string CS being processed is one single command group CG. Preferably command(s) is/are grouped into a command group CG by enclosing them by a pair of command group delimiters CGD, the master control device 1 verifying whether the command string CS it processes starts and ends with a pair of command group delimiters CGD. If this is the case then:

a.1) The master control device 1 recursively processes each command group CG within the command string CS simultaneously. The recursive nature of the processing of the command string CS by the master control device 1 will lead the process back to step a) above with the input command string CS being actually one of the command group(s) CG into which the command string CS within the single command group CG has been split up.

a.2) after step a.1) completed, the master control device 1 simultaneously transmits each command C within the command string CS (i.e. within the same command group CG) to the corresponding subsystem SB1-SBn to be carried out;

b) If the command string CS processed is not one single command group CG (i.e. the command string CS either comprises no command group CG or it comprises more than one different command groups CG, or a command group and one or more command(s) C), the master control device 1 is configured to sequentially process each command group(s) CG of the command string CS respectively transmit each command C of the command group CG being processed to the corresponding subsystem SB1-SBn for execution. In an exemplary embodiment, this sequential execution follows a left to right scheme.

To summarise: command(s) C and command group(s) CG contained within the same command group CG are processed/executed simultaneously (i.e. in parallel), while command(s) C and command group(s) CG not in the same command group are processed/executed sequentially (i.e. one after the other). Not in the same group might mean either part of different command group(s) CG or not part of a command group CG at all.

According to a preferred embodiment of the present invention each command group CG is enclosed by a pair of command group delimiters CGD. In this case the splitting of a command string CS into command group(s) is performed by identifying these command group delimiters CGD.

Furthermore each command C may be separated by a command delimiter CD and each subsystem(s) SB1-SBn identified by a subsystem identifier SI within the respective command C. Thus the splitting of a command string CS into command(s) C is performed by identifying these command delimiters CD and the commands are transmitted to a particular subsystem SB based on the subsystem identifier SI.

In a preferred embodiment, for carrying out a command C, each subsystem SB1-SBn is configured to sequentially execute all instruction(s) I within the command C, each instruction I being identified by an instruction identifier ID, each instruction I optionally comprising one or more instruction parameters IP.

In an even further embodiment, each subsystem SB1-SBn is configured such as to send a subsystem OK response back to the master control device 1 once all instruction(s) I within the command C have been successfully executed and to send a subsystem error response back to said master control device 1 immediately when an instruction I can not be executed successfully, preferably including its command delimiter CD and the instruction identifier ID that could not be executed optionally accompanied by an error code.

In an even further embodiment, in addition or alternatively to a subsystem OK response, each subsystem SB1-SBn is configured such as to raise events, each event triggering a response from the respective subsystem SB1-SBn to the master control device 1, each response comprising subsystem data such as values of measured parameters, status information of the subsystem, etc.

Each subsystem SB1-SBn may be configured to raise such events when particular conditions are met (such as a measured parameter being outside set boundary values).

Alternatively or in addition, each subsystem SB1-SBn may be configured to raise events at certain (pre-set or configurable by means of instruction parameters IP) intervals for streaming data to the master control device 1.

The master control device 1 may be configured such as to generate a system OK response once all commands C within the command string CS to be processed have been successfully carried out by the respective subsystem(s) SB1-SBn and to generate a system error response immediately when a subsystem error response is received.

According to a preferred embodiment of the present invention, the string of command(s) is represented by alphanumeric characters wherein:
- parentheses ( ) are used as a pair of command group delimiters CGD;
- a slash/used as command delimiter CD;
- each command C starts with a numerical subsystem identifier SI; and
- instructions I are identified by letters of the alphabet or special characters as instruction identifiers ID optionally followed by one or more instruction parameter(s) IP each delimited by a comma.

As a result, the grouping levels are represented as nested parentheses. In this embodiment the term "top level" group of a command string CS will mean consideration of the grouping by the outermost pair of parenthesis disregarding parenthesis within. For example the top level group of the command string "(/1Z(/3Z)/2Z)" is entire command string CS. The inner command group CG within this top level command group CG would be "(/3Z)". Also in this embodiment, the distinction whether command(s) and/or command group(s) are within the same command group is easily made by verifying whether these are within the same pair of parenthesis or not.

When referring to the inner command(s) C and/or command group(s) CG "within" a command group CG or command string CS, in this embodiment the collection of command(s) C and/or command group(s) CG shall be meant which is contained between the pair of parentheses delimiting the command string CS referred to.

In the following, the concept of the present invention shall be explained in detail with reference to this particularly advantageous representation of the string of commands and with reference to the exemplary laboratory system 100 of FIGS. 1 through 3B.

Assuming Z is the initialisation instruction, initializing subsystem SB1 will be represented by the following command:

/1Z

Upon completion of the initialisation, subsystem SB1 will provide a subsystem OK response back to the master control device 1. Concatenation of instructions I will allow the subsystem SB to execute multiple instructions I sequentially prior to sending back a response. The following command C example will initialize subsystem SB1 (instruction 'Z') followed by two absolute movements by parameters 50 respectively 100 assuming 'A' is the instruction identifier ID for absolute movements (instructions 'A100' and 'A50'):

/1ZA100A50

To address commands C to other subsystems SB, the same method is performed with different subsystem identifiers SI. As there is no need for predefined relationships among the subsystems SB within the laboratory system 100, the coordination of the subsystems SB can be defined dynamically by means of the command string CS transmitted to the master control device 1. An overall result of the processed respectively carried out/executed command string is reported back (preferably in the same format) by the master control device 1 as a system OK response thus eliminating multiple responses reported by the subsystems during the execution of the command string CS.

Figure 2:
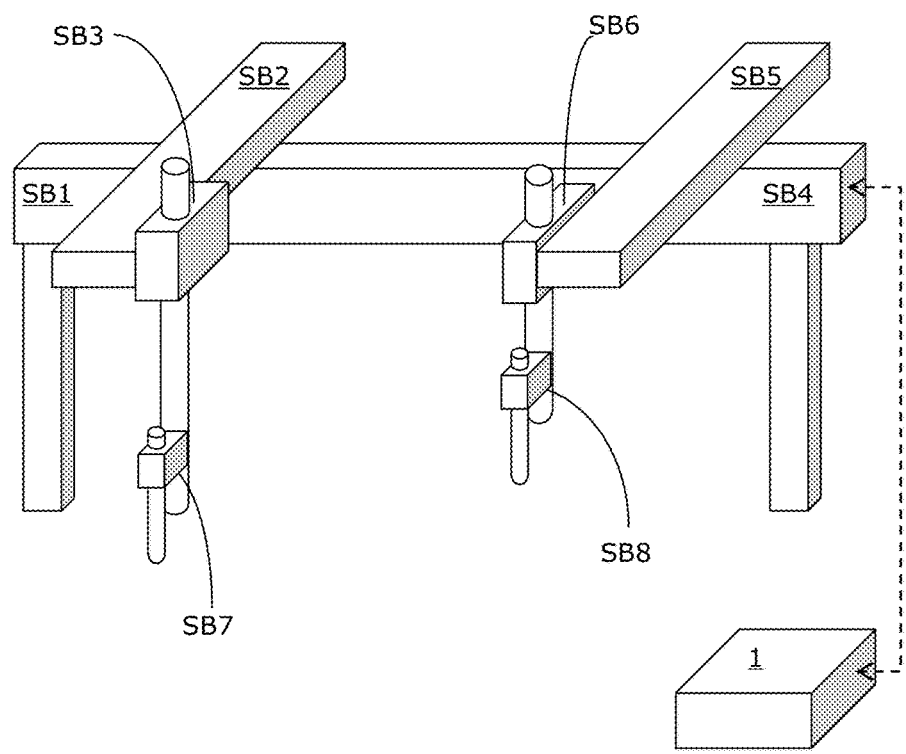
FIG. 2 a highly symbolic perspective representation of the exemplary laboratory system of FIG. 1.

FIGS. 1 and 2 show an exemplary robotic system as laboratory system 100 with six axes (subsystems SB1 through SB6) and two attached devices (subsystems SB7 and SB8). FIG. 1 shows a perspective view of such a laboratory system 100 while FIG. 2 depicts a symbolic representation of the same laboratory system 100.

To initialise the system 100 and avoid collisions into labware while doing so, axes 3 and 6, i.e. subsystems SB3 and SB6 are initialised simultaneously first and moved to their topmost positions. Axes 1 and 2 (subsystems SB1 and SB2) are initialised simultaneously after subsystem 3 completed the execution of the initialisation command. Analogously axes 4 and 5 (subsystems SB4 and SB5) are initialised simultaneously after subsystem 6 completed the execution of the initialisation command. Since SB3 and SB6 might have different initialising parameters, the elapsed time for SB3 and SB6 to complete the initialisation command may vary as well. Therefore subsystems SB1 and SB2 versus SB4 and SB5 are dealt with separately, i.e. their initialisation will be independent. Thus these can be carried out simultaneously.

Attached devices 7 and 8 (subsystems SB7 and SB8) are seen as different independent entities and thus initialised simultaneously during the initialisation of axes 3 and 6 (subsystems SB3 and SB6). The laboratory system 100 reports back a system OK response (indicating error-free processing of the command string CS, all commands C being successfully carried out by each subsystem SB and each instruction I within each command C being executed successfully).

The command string format according to the present invention—command string CS format which the laboratory system 100 is configured to process respectively execute respectively—utilizes grouping of commands C into command groups CS (the grouping being represented in the illustrated embodiment by a pair of parentheses) to define relations between the subsystems SB and thereby "encodes" the order and dependency of execution of each command C respectively instruction I.

The following command string CS example "encodes" the process to initialise axes 1 and 2 (SB1 and SB2) simultaneously where commands C in the same command group CG (here delimited by a pair of parentheses) are executed simultaneously:

(/1Z/2Z) or (/2Z/1Z)

Subsystems SB within different groups can have different execution priorities, thus to initialise axis 3 (SB3) prior to initialising the group of axes 1 and 2 (SB1 and SB2) would be "encoded" in the following command string CS:

(/3Z)(/1Z/2Z)

As the above command string CS does not consist of only one command group CG (in the depicted example this is apparent from the fact that the entire command string CS is not enclosed in a pair of parentheses) but comprises two different command groups CG, the command C '(/3Z)' and the command group CG '(/1Z/2Z)' will be processed sequentially as they belong to different command groups CG. In the illustrated exemplary embodiment, the order of processing/execution of command(s) C and/or command group(s) CG and/or instructions I within a command is from left to right. However any other scheme can be applied as long as the format of the command string CS is identical on the encoder and decoder side. Since there is only one subsystem SB3 in the first group, the above command string CS can be abbreviated to:

/3Z(/1Z/2Z)

As in the above command string the command '/3Z' and the command group '(/1Z/2Z)' are not within the same command group CG (the first not belonging to any command group at all), the command '/3Z' and the command group '(/1Z/2Z)' are executed sequentially.

The command group delimiters CGD (in the illustrated example a pair of parentheses) impose the execution priority similar to the mathematical order of execution imposed by parentheses. Since the inner "nested" command group CG has a higher execution priority (since within the same command group CG command group(s) CG are executed prior to command(s) C, the above command string can also be written as:

((/3Z)/1Z/2Z)

In this case, as the command string CS consists of only one command group CG (in the depicted example this is apparent from the fact that the entire command string CS is enclosed in a pair of parentheses), the command groups CG within the "inner" command string CS (i.e. the command string CS within the pair of command group delimiters CGS) are processed before the simultaneous transmission of the command(s) C to SB1 respectively SB2. Since within the same command group CG there is no sequentiality, the above command string CS can be also written as:

(/1Z(/3Z)/2Z) or (/1Z/2Z(/3Z))

The above exemplary command string CS encodes the initialisation of SB3 prior to simultaneously initialising SB1 and SB2. Based on the same concept, the same can be applied to SB6 prior to SB4 and SB5 as:

((/6Z)/4Z/5Z) or (/4Z(/6Z)/5Z) or (/4Z/5Z(/6Z))

Concatenating the two results in the sequence of sequentially initialising groups of axes (subsystems) SB1, SB2 and SB3 and group of axes (subsystems) SB4, SB5 and SB6 (sequentiality due to the respective inner command groups belonging to different "top level" command groups):

((/3Z)/1Z/2Z) ((/6Z)/4Z/5Z)

Figure 3A:
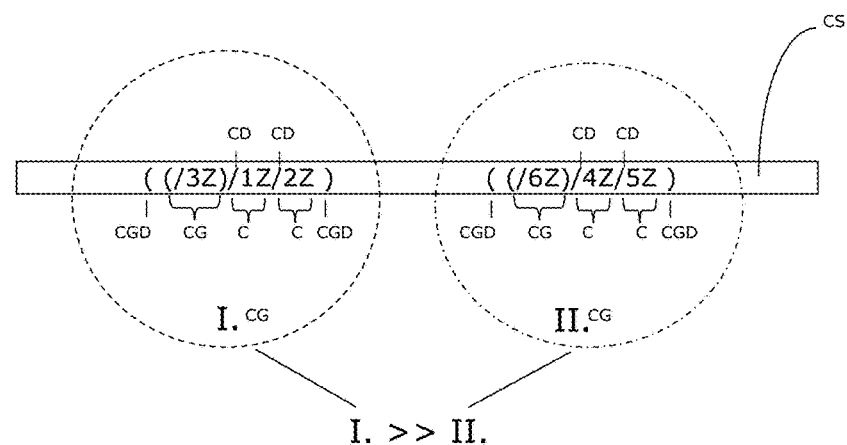
FIG. 3A an illustrative representation of a command string according to the present invention, the command string comprising two command groups to be executed sequentially.

The concept of the above command string CS is illustrated on FIG. 3A, with the command groups I. CG and II. CG "of the" command string CS not of the same command group being encircled with dashed, respectively dotted-dashed lines and the entire command string CS being surrounded by a rectangle. The sequential execution of command groups I. CG and II. CG. "of the" command string CS is illustrated by the use of the symbols ">>".

In order to impose simultaneous/parallel initialisation of groups of axes SB1, SB2 and SB3 and group of axes SB4, SB5 and SB6, the two corresponding command groups I. CG and II.CG are grouped into the same command group CG:

((((/3Z)/1Z/2Z) ((/6Z)/4Z/5Z))

Note: extra spaces are inserted into the strings as illustrated to emphasise the different command groups.

Figure 3B:
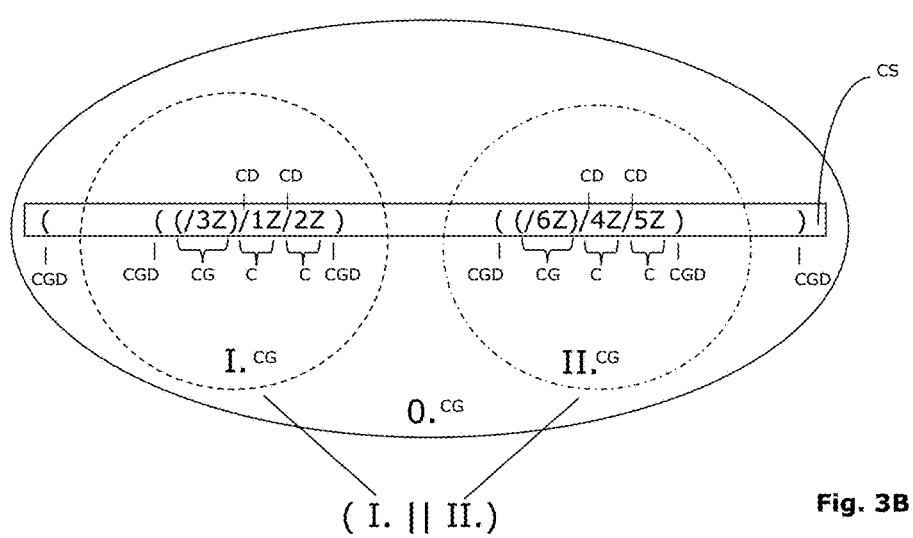
FIG. 3B an illustrative representation of a command string according to the present invention, the command string consisting of one command group, said command group itself comprising two command groups within to be executed simultaneously.

The concept of the above command string CS is illustrated on FIG. 3B, with the command groups I.CG and II.CG. of the same command group CG being encircled with dashed, respectively dotted-dashed lines. As seen on this figure, the entire command string CS consists of only one command group 0.CG (encircled with a continuous line). As command groups I.CG and II.CG of FIG. 3B are within the same command group 0.CG, they are processed simultaneously. The simultaneous execution of command groups I.CG and II.CG. "within" the command string CS is illustrated by the use of the symbols "||".

Transmission of the above command string CS to the laboratory system 100 of the present invention will first simultaneously initialise axes SB3 and SB 6. Since SB1 and SB2 versus SB4 and SB5 are in different groups, the initialisation of SB1 and SB2 does not need to follow (i.e. be sequential to) the initialisation of SB6 and vice versa.

Combined with the simultaneous initialisation of independent attached devices 7 and 8 (SB7 and SB8), the overall initialisation can be "encoded" into the following command string CS:

((((/3Z)/1Z/2Z) ((/6Z)/4Z/5Z) (/7Z/8Z))

Once can clearly see that the above command string CS as a whole consists of only one "top level" command group CG (apparent from the fact that the entire command string CS is enclosed in a pair of parentheses). Therefore all "inner" command groups CG within the entire command string CS are processed simultaneously, i.e. command groups '((/3Z)/1Z/2Z)' and '((/6Z)/4Z/5Z)' and '(/7Z/8Z)' are processed simultaneously as they are all within the same "top level" command group CG. As the initialisation commands of SB3 and SB6 each form a command group CG themselves, these command groups CG (command groups CG comprising only one command C, which in turn comprises only one instruction I) are processed first.

After the command string CS for initialising the system 100, a command string CS for a subsequent 6-axis simultaneous movement can be appended:

((((/3Z)/1Z/2Z)((/6Z)/4Z/5Z)(/7Z/8Z))  (/1A10/2A10/3A20/4A10/5A20/6A20)

Figure 3C:
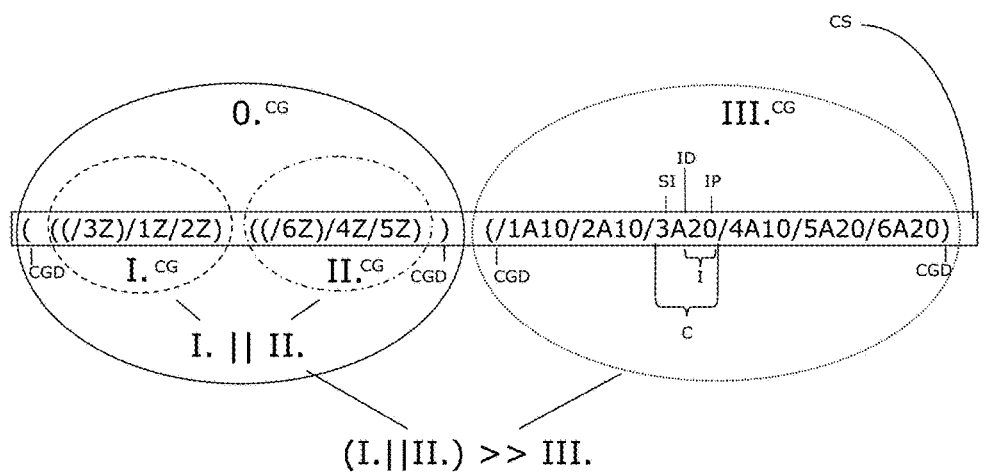
FIG. 3C an illustrative representation of a command string according to the present invention, the command string comprising two command groups to be executed sequentially one after another, the first command group itself comprising two command groups within to be executed simultaneously, while the latter comprising multiple commands to be executed simultaneously.

The concept of the above command string CS is illustrated on FIG. 3C, with the command groups I.CG and II.CG. encircled with dashed, respectively dotted-dashed lines, within the same command group 0.CG encircled in continuous line and sequentially subsequent command group III.CG (for the 6-axis simultaneous movement as corresponding commands C are within the same command group III.CG) being encircled with dotted lines.

As it can be seen above and in FIG. 3C, the entire command string CS comprises two "top level" command groups 0.CG and III.CG, the former command group 0.CG representing the initialisation comprising two "inner" command groups I.CG and II.CG processed simultaneously, the latter command group III.CG of the command string CS representing the subsequent 6-axis movement. Therefore (since 0.CG and III.CG are not in the same command group CG) the initialisation and the 6-axis simultaneous movement is carried out sequentially illustrated by the use of the symbols ">>".

Other than initialisation and motion related commands C, for example report commands C can also be grouped thus creating a mixture of coordinated motion and response from the subsystems SB.

Figure 4:
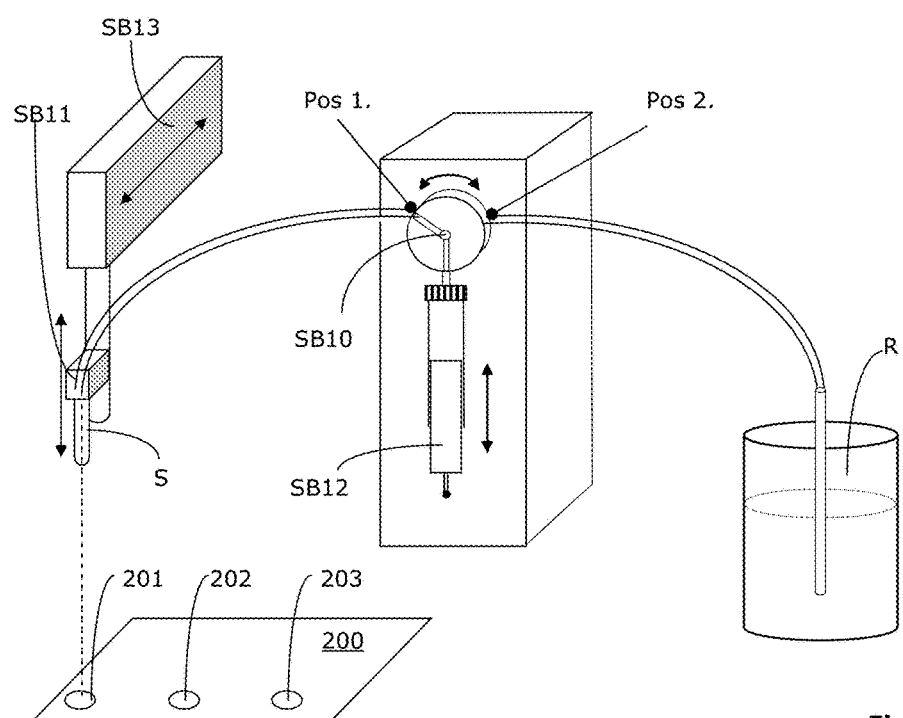
FIG. 4 a highly symbolic perspective representation of a dilutor system as a further exemplary laboratory system according to the present invention.

As a further example of a laboratory system of the present invention, FIG. 4 depicts a highly symbolic perspective representation of a dilutor system comprising a 3-way valve as subsystem SB10, a linear actuator as subsystem SB11 for moving a syringe of the dilutor up and down, a pump as subsystem SB12; a reservoir R and a linear actuator as subsystem SB13 for moving the syringe S from between wells 201-203 of a sample plate 200.

For the dilutor system of FIG. 4, the following process:
Simultaneous initialization (instruction "Z") of all subsystems SB10 to SB12;
Simultaneously setting the 3-way valve SB10 into position Pos. 1 (instruction "S" with instruction parameter "1") and lowering the syringe S (instruction "A" of SB11 by parameter "10");
Aspiration of 5 ml samples via the syringe S (by instruction "P" with parameter "5" to the pump SB12);
Raising the syringe S (instruction "A" of SB11 by parameter "-10");
Moving the syringe S from well 201 to well 202 of the sample plate (instruction "M" with parameter "2" to SB13);
Lowering the syringe S (instruction "A" of SB11 by parameter "10");
Dispensing of 5 ml samples via the syringe S (by instruction "D" with parameter "5" to the pump SB12);
Setting the 3-way valve SB10 into position Pos. 2 (instruction "S" with instruction parameter "2");
Simultaneous aspiration of 15 ml liquid from the reservoir (by instruction "P" with parameter "15" to the pump SB12) and
raising the syringe S (instruction "A" of SB11 by parameter "-10");
then moving the syringe S from well 202 to well 203 of the sample plate (instruction "M" with parameter "3" to SB13);
then lowering the syringe S into well 203 (instruction "A" of SB11 by parameter "10");
Setting the 3-way valve SB10 into position Pos. 1 (instruction "S" with instruction parameter "1");
Flushing the syringe S with the 15 ml system liquid into well 203 (by instruction "D" with parameter "15" to the pump SB12). could be "encoded" according to the present invention into the following command string CS:
(/10Z/11Z/12Z/13Z)
(/10S1/11A10)
(/12P5)
(/11A-10)
(/13M2)
(/11A10)
(/12D5)
(/10S2)
((/12P15) ((((/11A-10)/13M3)/11A10)
(/10S1)
(/12D15)

Note: The above command string CS has been split into separated lines; extra spaces have been introduced and bold resp. italics have been used to ease the identification of the command groups associated with each step of the process above.

As an example for a further embodiment of the present invention, wherein each subsystem SB1-SBn is configured such as to be able to raise events, and to illustrate streaming of data from a subsystem to the master control device 1, the following command C to subsystem SB8 enables pressure monitoring and performs liquid aspiration where 'o' is a configuration instruction with 2 instruction parameters IP and instruction 'P' is to absorb 1000 increments of liquid:

/8o0,1P1000

The above command C "/8o0,1P1000" comprises two instructions "o0,1" and "P1000" which are executed sequentially. Once "o0,1" is executed, pressure monitoring is enabled and then the instruction for aspiration of 1000 increments of liquid is executed. One should note that the instruction "o0,1" is not for executing the pressure monitoring but for enabling pressure monitoring. Therefore the next instruction "P1000" (absorption) is carried out immediately after pressure monitoring has been enabled and not after pressure monitoring is completed/finished. After the execution of the above command C, a "stream" of responses such as below (assuming "!" is the instruction identifier ID for events) are sent from subsystem SB8 to the master control device 1 (only a portion of the response is listed here as pressure monitoring continues until a command C comprising a corresponding instruction I to disable pressure monitoring is sent to the subsystem SB8):

!033FF8DFF8DFF8D
!033FF8CFF8BFF8B
!033FF8BFF8CFF8D
!033FF8DFF8BFF8D
!033FF8FFF8FFF8B
!033FF8EFF8FFF8D
!033FF8DFF8CFF8A
!033FF8DFF8DFF8E
!033FF8FFF8EFF8F
!033FF8DFF8CFF8E
!033FF8DFF8BFF8E
!033FF8CFF8EFF8C
!033FF8BFF8DFF8E
!033FF90FF91FF8B
!033FF8DFF8DFF8F
!033FF8DFF8DFF8E
!033FF8BFF8BFF8D
!033FF8DFF8CFF8D
!033FF8CFF8DFF8C
!033FF8EFF8FFF8E
!033FF8DFF8DFF8C
!033FF8DFF8CFF8C
!033FF8CFF8CFF8F
!033FF8CFF8DFF8F
!033FF8EFF8DFF8E

It will be understood that many variations could be adopted based on the specific structure hereinbefore described without departing from the scope of the invention as defined in the following claims.

REFERENCE LIST laboratory system 100
master control device 1
subsystems SB1-SBn
command C
instruction I
instruction identifier ID
command group CG
command group delimiter CGD
command delimiter CD
subsystem identifier SI
instruction parameter IP
Reservoir R
Sample plate 200
Wells (of the sample plate) 201-203

The invention claimed is:

1. A laboratory system (100) comprising:
    multiple subsystems (SB1-SBn), each comprising at least one of diluters, actuators, sensors, pumps, indicating devices, and robotic arms, or a combination thereof, and configured to receive and carry out a command (C); and
    a master control device (1) configured to process a command string (CS) and to transmit commands (C) to a corresponding subsystem (SB1-SBn),
    wherein said command string (CS) comprises at least one of:
        one or more commands (C), and
        one or more command groups (CG), and
    wherein each command group (CG) comprises at least one of:
        one or more commands (C), and
        one or more command groups (CG), and
    wherein at least one of:
        one or more commands (C), and
        one or more command groups (CG)
    can be nested on multiple levels of grouping in the command string (CS),
    wherein one or more commands (C) and one or more command groups (CG) with higher execution priority are grouped into respective command groups (CG) in the command string (CS), and
    wherein one or more commands (C) and one or more of said respective command groups (CG) are concatenated to form said command string (CS), and
    wherein the master control device (1) is configured:
        to simultaneously process the one or more commands (C) and the one or more command groups (CG) comprised within the same command group (CG) prior to simultaneously transmitting the commands (C) comprised within the same command group (CG) to the corresponding subsystem (SB1-SBn), and
        to sequentially process one or more commands (C) and one or more command groups (CG) not comprised within the same command group (CG) and to sequentially transmit the commands (C) not comprised within the same command group (CG) to the corresponding subsystem (SB1-SBn), and
    wherein a command group (CG), which is nested within a certain command group (CG), has a higher execution priority and is executed prior to a command (C) comprised within said certain command group (CG), and
    wherein the master control device (1) is further configured to process said command string (CS) in a recursive manner, each time going one level inside the nested group of commands (CG) and transmitting individual commands (C) to the corresponding subsystem (SB1-SBn) when a level is reached where the commands (C) are not grouped.

2. A laboratory system (100) according to claim 1, wherein each command group (CG) is enclosed by a pair of command group delimiters (CGD).

3. A laboratory system (100) according to claim 2, wherein:
    each command (C) is separated by a command delimiter (CD); and
    each subsystem (SB1-SBn) is identified by a subsystem identifier (SI) within the respective command (C).

4. A laboratory system (100) according to claim 3, wherein the master control device (1) is configured to split the command string (CS) into one or more command croup (CG) and one or more command (C) based on each command group (CG) being enclosed by a pair of command group delimiters (CGD) and commands (C) being separated by a command delimiter (CD).

5. A laboratory system (100) according to claim 4, wherein, for carrying out said command (C), each subsystem (SB1-SBn) is configured to sequentially execute all instruction (I) within the command (C), each instruction (I) being identified by an instruction identifier (ID).

6. A laboratory system (100) according to claim 5, wherein each subsystem (SB1-SBn) is configured such as to send a subsystem OK response back to said master control device (1) once all instruction (I) within the command (C) have been successfully executed and to send a subsystem error response back to said master control device (1) immediately when an instruction (I) cannot be executed successfully.

7. A laboratory system (100) according to claim 5, wherein each subsystem (SB1-SBn) is configurable to raise one or more events by means of a corresponding instruction (I) to do so, each event triggering a response from the respective subsystem (SB1-SBn) to the master control device (1), each response comprising subsystem data.

8. A laboratory system (100) according to claim 7, wherein each subsystem (SB1-SBn) is configurable to raise said events at pre-set or at configurable intervals of time for streaming subsystem data from the respective subsystem (SB1-SBn) to the master control device (1).

9. A laboratory system (100) according to claim 6, wherein said master control device (1) is configured such as to generate a system OK response once all commands (C) within the command string (CS) to be processed have been successfully carried out by the respective subsystem (SB1-SBn) and to generate a system error response immediately when a subsystem error response is received.

10. A laboratory system (100) according to claim 1, wherein the sequence of sequentially processed command group (CG) respectively command (C) transmitted to the corresponding subsystem (SB1-SBn) is determined based on the command string (CS) being processed according to either of the following schemes:
first in first out FIFO;
last in first out LIFO;
left to right; or
right to left.

11. A method for controlling a laboratory system (100) comprising multiple subsystems (SB1-SBn), each comprising at least one of diluters, actuators, sensors, pumps, indicating devices, and robotic arms, or a combination thereof, and configured to receive and carry out a command (C), and a master control device (1) configured to process a command string (CS),
wherein said command string (CS) comprises at least one of:
one or more commands (C), and
one or more command groups (CG), and
wherein each command group (CG) comprises at least one of:
one or more commands (C), and
one or more command groups (CG), and
wherein at least one of:
one or more commands (C), and
one or more command groups (CS)
can be nested on multiple levels of grouping in the command string (CS),
the method comprising the steps of:
I) grouping one or more commands (C) and one or more command groups (CG) with higher execution priority into respective command groups (CG) in the command string (CS),
II) concatenating one or more commands (C) and one or more of said respective command groups (CG) to form said command string (CS),
III) simultaneously processing the one or more commands (C) and the one or more command groups (CG) comprised within the same command group (CG) prior to simultaneously transmitting the commands (C) comprised within the same command group (CG) to the corresponding subsystem (SB1-SBn), and
IV) sequentially processing one or more commands (C) and one or more command groups (CG) not comprised within the same command group (CG) and sequentially transmitting the commands (C) not comprised within the same command group (CG) to the corresponding subsystem (SB1-SBn),
wherein a command group (CG), which is nested within a certain command group (CG), has a higher execution priority and is executed prior to a command (C) comprised within said certain command group (CG), and
wherein said command string (CS) is processed in a recursive manner by said master control device (1), each time going one level inside the nested groups of commands (CG) and transmitting individual commands (C) to the corresponding subsystem (SB1-SBn) when a level is reached where the commands (C) are not grouped.

12. A method for controlling a laboratory system (100) according to claim 11, further comprising the step of transmitting the command string (CS) comprising at least one of:
one or more command (C), and
one or more command group (CG)
to the master control device (1) of the laboratory system (100) to be processed.

13. A method for controlling a laboratory system (100) according to claim 12, wherein the step of grouping one or more command (C) respectively one or more command group (CG) into a command group (CG) comprises the step of enclosing said one or more command (C) respectively said one or more command group (CG) by a pair of command group delimiters (CGD).

14. A method for controlling a laboratory system (100) according to claim 13 further comprising the steps of:
separating each command (C) by a command delimiter (CD); and
identifying each subsystem (SB1-SBn) to carry out a command (C) by a subsystem identifier (SI) within the respective command (C).

15. A method for controlling a laboratory system (100) according to claim 14, further comprising the steps of:
concatenating all instructions (I) to be sequentially executed by a subsystem (SB1-SBn) into a respective command (C); and
identifying each instruction (I) to be executed by a subsystem (SB1-SBn) by an instruction identifier (ID).

* * * * *

UNITED STATES PATENT AND TRADEMARK OFFICE
CERTIFICATE OF CORRECTION

PATENT NO. : 9,823,628 B2
APPLICATION NO. : 13/739455
DATED : November 21, 2017
INVENTOR(S) : Mark Ma Page 1 of 1

It is certified that error appears in the above-identified patent and that said Letters Patent is hereby corrected as shown below:

On the Title Page

(54) should read:
-- LABORATORY SYSTEM HAVING MULTIPLE SUBSYSTEMS AND A MASTER CONTROL DEVICE TRANSMITTING NESTED COMMANDS --

Signed and Sealed this
Fifteenth Day of May, 2018

Andrei Iancu
*Director of the United States Patent and Trademark Office*